United States Patent
Lanzetta

(10) Patent No.: US 10,231,841 B2
(45) Date of Patent: Mar. 19, 2019

(54) PROSTHESIS FOR THE TRAPEZE-METACARPAL JOINT OF THE THUMB

(71) Applicant: Marco Lanzetta, Ruvigliana (CH)

(72) Inventor: Marco Lanzetta, Ruvigliana (CH)

( * ) Notice: Subject to any disclaimer, the term of this patent is extended or adjusted under 35 U.S.C. 154(b) by 0 days.

(21) Appl. No.: 15/558,577

(22) PCT Filed: Apr. 7, 2016

(86) PCT No.: PCT/IB2016/051974
§ 371 (c)(1),
(2) Date: Sep. 15, 2017

(87) PCT Pub. No.: WO2016/166641
PCT Pub. Date: Oct. 20, 2016

(65) Prior Publication Data
US 2018/0049882 A1    Feb. 22, 2018

(30) Foreign Application Priority Data

Apr. 13, 2015  (IT) .............................. MI2015A0522

(51) Int. Cl.
*A61F 2/42*     (2006.01)
*A61B 17/84*    (2006.01)
*A61F 2/30*     (2006.01)

(52) U.S. Cl.
CPC .......... *A61F 2/4261* (2013.01); *A61B 17/842* (2013.01); *A61F 2002/3028* (2013.01); *A61F 2002/30242* (2013.01); *A61F 2002/30578* (2013.01); *A61F 2002/30754* (2013.01); *A61F 2002/30909* (2013.01); *A61F 2002/4258* (2013.01); *A61F 2002/4276* (2013.01)

(58) Field of Classification Search
CPC ...... A61F 2002/4258; A61F 2002/4276; A61F 2002/3028; A61F 2/4261; A61F 2002/30754; A61F 2002/30909
See application file for complete search history.

(56) References Cited

U.S. PATENT DOCUMENTS

2007/0021839 A1  1/2007  Lowe
2013/0226306 A1  8/2013  Naidu

FOREIGN PATENT DOCUMENTS

EP   1112753        7/2001
FR   2801194        5/2001
WO   WO2010097724   9/2010

*Primary Examiner* — David H Willse
*Assistant Examiner* — Javier Blanco
(74) *Attorney, Agent, or Firm* — King & Schickli, PLLC

(57) ABSTRACT

A prosthesis (1) for the trapeze-metacarpal joint of the thumb comprises a body (2) suitable for being arranged between the scaphoid (31) and the metacarpus (30) of the thumb, such body (2) has the shape of an Archimedean solid and operates as a spacer between the scaphoid (31) and the metacarpus (30).

5 Claims, 7 Drawing Sheets

PROSTHESIS FOR THE TRAPEZE-METACARPAL JOINT OF THE THUMB

The present invention relates to a prosthesis for the trapeze-metacarpal joint of the thumb, according to the preamble of the main claim.

SUMMARY OF THE INVENTION

It is known that the arthrosis of the trapeze-metacarpal joint is a disease that determines a progressive deterioration of such joint and limits the use of the hand and above all of the thumb in the normal personal and working activities. All of this with a pain associated with.

This disease can be treated with drugs, but in the most important forms of arthrosis there is a need for operating the hand surgically.

A possible operation that offers very good results is that which implies the total removal of the trapezium and its replacement with a spacer, made from a biocompatible material, operating as a prosthesis for the trapeze-metacarpal joint of the thumb and having the purpose of stabilizing the relative position between the scaphoid and the metacarpus.

EP1112753 describes an implant to be interposed between two movable bone surfaces made from a material comprising pyrocarbon and devoid of any means of fixing to the bones between which the implant is arranged. This patent document describes a variety of embodiments of the implant which always present continuous and rounded surfaces in any case. This solution does not assure an optimum fixing of the implant to the bones because of the presence of such rounded surfaces.

US2013/0226306 describes an implant made from polycarbonate urethane suitable for being arranged between bones and supporting compressing and shear forces. A variety of embodiments of this invention are described in this patent document of the prior art; most of such embodiments comprise a body suitable for being interposed between adjacent bones and from which a pin projects suitable for being inserted into a bore formed in a bone. Embodiments are also described wherein such pin is not provided, but just a body interposed between the adjacent bones; such body can have shapes with concave and/or convex and/or flat surfaces which co-operate with corresponding surfaces obtained by operating onto the bones and shaping them in an appropriate way to perfectly get in contact with the surfaces of the implant. In order to use the implant according to document US2013/0226306, it is necessary to operate onto the patient's bones to prepare them to the co-operation with the surfaces and/or the stem of the implant. Wherever no stem is provided, the body of the implant is fixed hardly to the bones facing thereto which might result in an undesired offset between the bones and between the bones and the implant.

An object of the present invention is to provide a prosthesis of the mentioned type that is enhanced with respect to the known prosthesis and allows an optimum stabilization of the base of the metacarpus with respect to the scaphoid.

Another object is to provide a prosthesis of the mentioned type whose insertion into the hand can be obtained in a simpler manner than those used to arrange the known prosthesis in replacement of the trapezium.

A further object is to provide a prosthesis that can be quickly incorporated in the tissue of the hand.

Another object is to provide a prosthesis that is identifiable during a X-ray examination.

These objects and others that will be apparent to those skilled in this sector are achieved by a prosthesis according to the attached claims.

BRIEF DESCRIPTION OF THE DRAWING FIGURES

For a better understanding of the present invention the following drawings are attached for merely explanatory, hence non limitative, purposes, wherein.

DETAILED DESCRIPTION OF THE INVENTION

Figure 1:
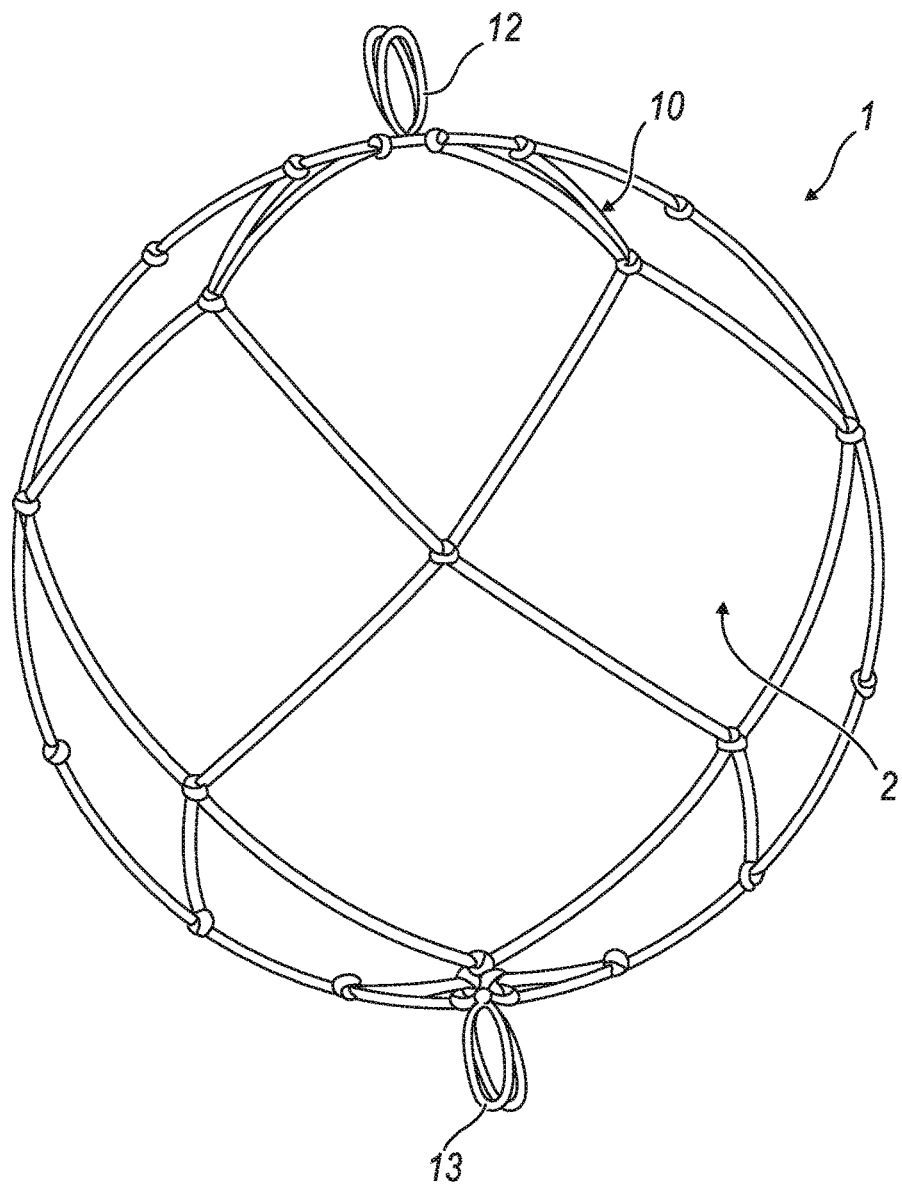
FIG. 1 shows a front view of a prosthesis according to the invention.
Figure 2:
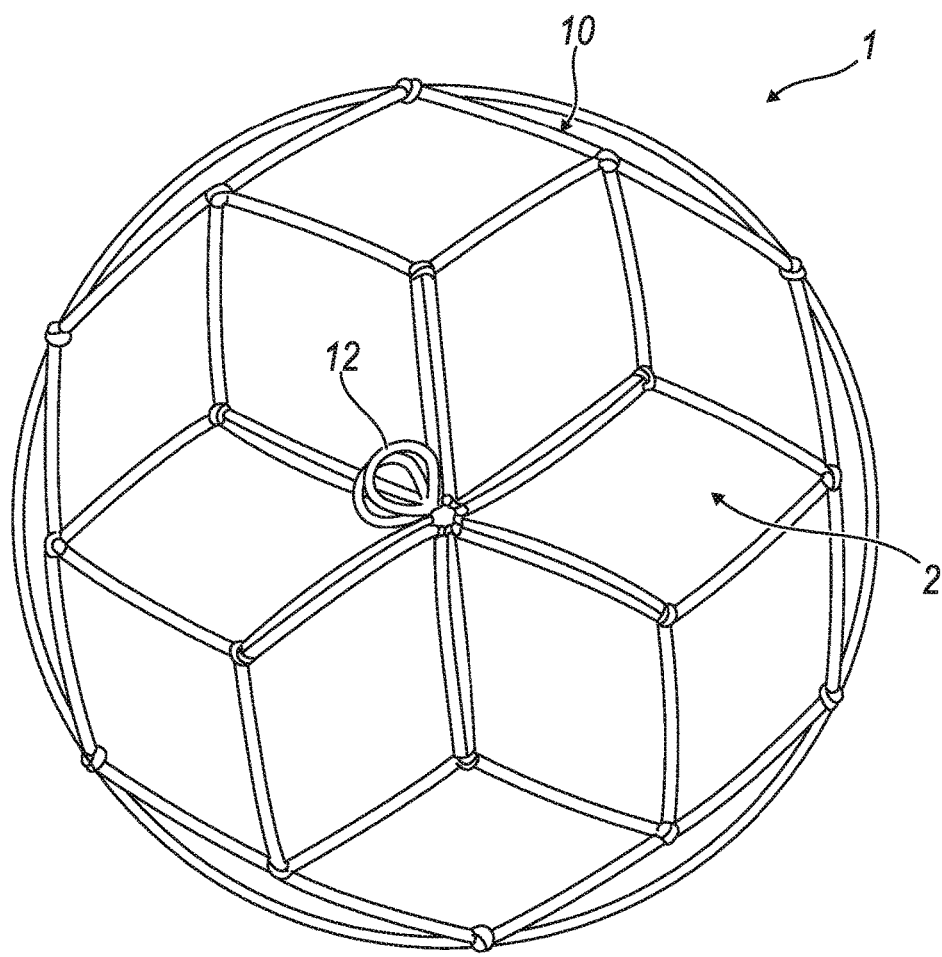
FIG. 2 shows a top view of the prosthesis in FIG. 1.
Figure 3:
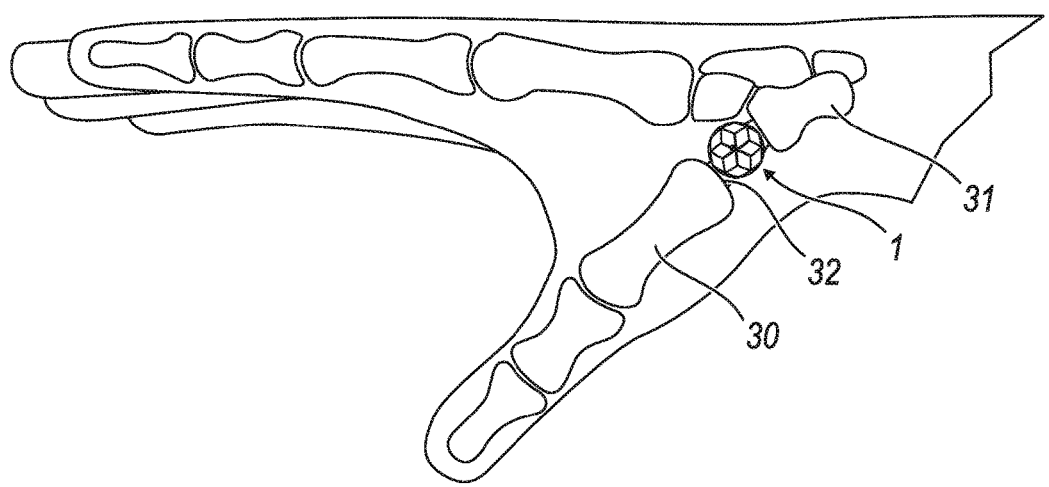
FIG. 3 shows a schematic transparent view of a hand in which the prosthesis in FIG. 3 is inserted.

In the attached figures, identical or corresponding parts are identified by the same reference numerals.

With reference to FIGS. 1-4, they show a first embodiment of the invention wherein the prosthesis is generically referred to with the reference numeral 1 and comprises a solid body 2 made of a biocompatible material. For instance, the latter can be made of Goretex, Dacron, or PTFE.

Figure 4:
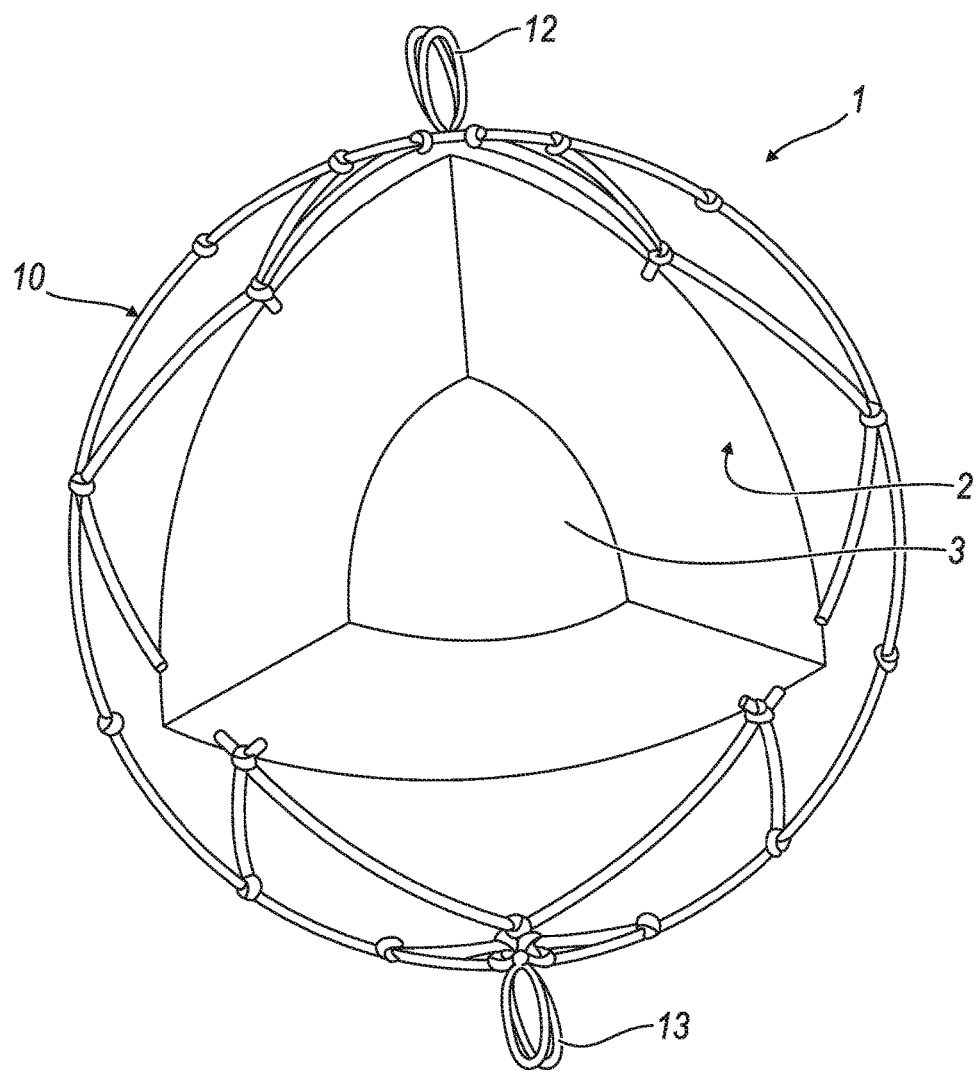
FIG. 4 shows a perspective view of the prosthesis in FIG. 1, a portion being cutaway for the sake of clearness.

The body 2 might include, as shown in FIG. 4, a metal core 3 suitable for making the prosthesis 1 visible in a X-ray examination.

Such body 2 has the shape of an Archimedean solid and such as to "occupy" at best the space that is occupied by the trapezium in the hand. During a surgical operation, whenever such bone (trapezium) is removed from the hand, a substantially cubic space is created which is just filled at best by the shape of the Archimedean solid of the prosthesis. The body 2 is thus positioned between the metacarpus 30 and the scaphoid 31 of the hand and operates as a spacer between these bones; the base 32 of the metacarpus 30 rests thereupon.

Advantageously the body 2 is wound by a non absorbable thread 10 for instance made from nylon, prolene, or another material that facilitates the incorporation and the fixing of the body 2 in the tissue of the hand so as to stimulate the fibrous response of the body or of the surrounding tissue.

In order to fix the body in position, such net includes at least two eyelets or eyes 12 and 13, located in opposed positions, through which it is possible to make one or more suture threads (not shown), preferably of a non absorbable type, pass through around tendon or capsule structures in order to anchor the prosthesis 1 therebetween.

The net 10 can include more than two eyelets indeed to constrain the prosthesis to the bones of the hand too.

Figure 5:
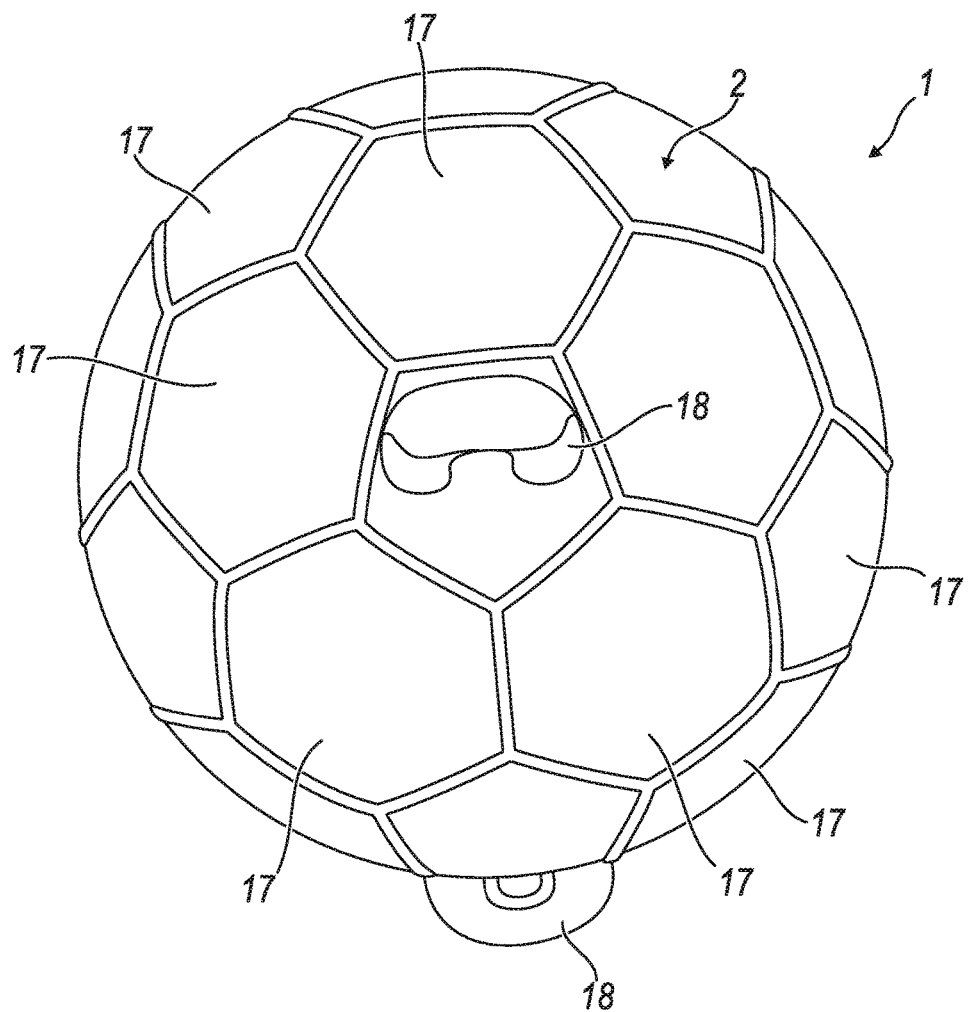
FIG. 5 shows a front view of a variant of the prosthesis in FIG. 1.
Figure 6:
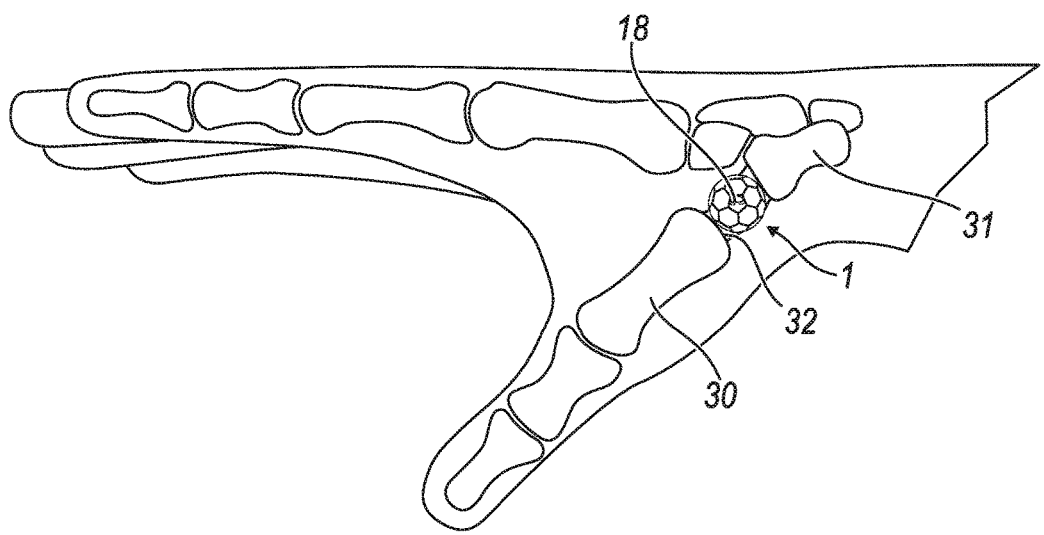
FIG. 6 shows a schematic transparent view of a hand in which the prosthesis in FIG. 5 is inserted.
Figure 7:
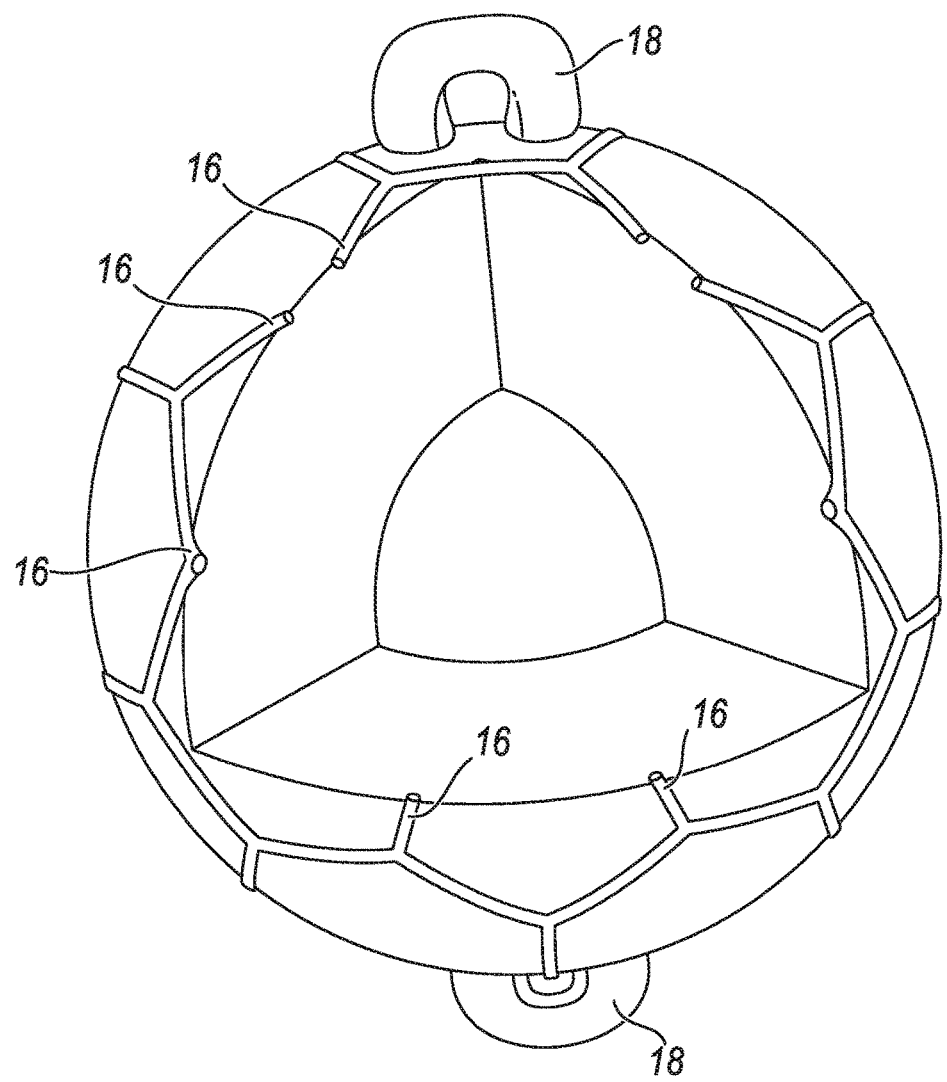
FIG. 7 shows a perspective view of the prosthesis in FIG. 5, a portion being cutaway for the sake of clearness.

In FIGS. 5, 6, and 7, the prosthesis 1 has the shape of a regular icosahedron, i.e. a solid body featuring a plurality of facets. The body here considered can have surface grooves 16 between the individual hexagonal and pentagonal faces 17 of the prosthesis, or not; in such grooves or in any case on the surface of the body 2 there is placed a net or grid 10

(for instance made from nylon or prolene) as with the embodiment shown in FIGS. 1-4.

The prosthesis 1 also includes a number of projecting eyelets 18, integral with the body 2, for constraining (by means of a suture thread) the prosthesis to the tendon or capsule structures.

The solution illustrated in FIG. 5 can also have a metal core in order to make the prosthesis detectable with a X-ray examination.

The insertion of the prosthesis 1 into the hand takes place in a way similar to that already described with respect to FIGS. 1-4, hence such insertion mode is not further described.

Thanks to its shape, the prosthesis 1 is easily insertable into the hand in the space cleared upon removing the trapezium. As a matter of fact, no preferred direction exist for such insertion because the body 2 has the shape of an Archimedean solid which does not have any preferred part for getting in contact with the adjacent bones. Its faceted shape guarantees a limited slip onto the surfaces of the adjacent bones (which do not necessarily require a surface treatment to co-operate with those of the prosthesis); this occurs thanks to the greater friction generated between the flat faces of the prosthesis and the bones as referred to the friction that is generated between the curved surfaces of the prosthesis according to the status of the art and the bones.

Furthermore, such body is easy to handle and, thanks to the net-like configuration of the part (net 10) that winds it, it can be easily incorporated into the adjacent periprosthesic tissues. As a matter of fact, such net or grid 10 stimulates a fibrous proliferation of the body that receives the prosthesis, hence anchoring and strength as well as the incorporation and the prosthesic strength of the implant in the replacement area.

Various embodiments of the invention have been described. However, others are considered to be obtainable on the basis of the previous description: for instance, the body 2 might have a number of facets different from those of the icosahedron, while retaining a shape of various and known Archimedean solids. Such variants of the invention shall also to be considered to fall within the scope of the following claims.

The invention claimed is:

1. A trapezium prosthesis (1) for the trapezio-metacarpal joint of the thumb, said trapezium prosthesis (1) comprising a solid body (2) having an inner core (3), said solid body (2) suitable for being arranged between the scaphoid (31) and the metacarpus (30) of the thumb, said solid body being suitable for operating as a spacer between said scaphoid (31) and metacarpus (30), characterized in that the solid body (2) has the shape of an Archimedean solid having a plurality of facets (17),
wherein the solid body (2) is provided with surface grooves (16) between the facets (17),
wherein a net or grid (10) is wrapped around the solid body (2), and wherein portions of said net or grid (10) are inserted into the surface grooves (16) of the solid body (2), and
wherein the trapezium prosthesis further comprises fixing means (13, 18) suitable for allowing a constraint of the solid body (2) to the scaphoid (31) and the metacarpus (30).

2. A trapezium prosthesis according to claim 1, wherein said net or grid (10) comprises a non absorbable thread, said non absorbable thread made from a material selected from the group consisting of prolene or nylon.

3. A trapezium prosthesis according to claim 1, wherein said body is made of a material selected from the group consisting of Goretex, Dacron, or PTFE.

4. A trapezium prosthesis according to claim 1, wherein said fixing means comprises at least two eyelets (13) projecting from said net or grid (10) or, alternatively, at least two eyelets (18) projecting directly from the solid body (2) of the prosthesis and integral therewith.

5. A trapezium prosthesis according to claim 1, wherein the solid body (2) has the shape of an icosahedron.

* * * * *